US006582431B1

(12) United States Patent
Ray

(10) Patent No.: US 6,582,431 B1
(45) Date of Patent: Jun. 24, 2003

(54) EXPANDABLE NON-THREADED SPINAL FUSION DEVICE

(75) Inventor: Charles Dean Ray, Williamsburg, VA (US)

(73) Assignee: Howmedica Osteonics Corp., Allendale, NJ (US)

( * ) Notice: Subject to any disclaimer, the term of this patent is extended or adjusted under 35 U.S.C. 154(b) by 0 days.

(21) Appl. No.: 09/436,955

(22) Filed: Nov. 5, 1999

Related U.S. Application Data

(63) Continuation of application No. PCT/US99/02148, filed on Feb. 6, 1998.
(60) Provisional application No. 60/037,458, filed on Feb. 6, 1997.

(51) Int. Cl.[7] .............................................. A61B 17/70
(52) U.S. Cl. ...................... 606/61; 623/17.16
(58) Field of Search ................... 606/60, 61, 71, 606/72, 73, 75; 623/17.11, 17.15, 17.16

(56) References Cited

U.S. PATENT DOCUMENTS

| 3,916,907 | A | | 11/1975 | Peterson |
| 4,961,740 | A | | 10/1990 | Ray et al. |
| 5,059,193 | A | | 10/1991 | Kuslich |
| 5,122,130 | A | | 6/1992 | Keller |
| 5,458,638 | A | | 10/1995 | Kuslich et al. |
| 5,489,307 | A | | 2/1996 | Kuslich et al. |
| 5,609,636 | A | | 3/1997 | Kohrs et al. |
| D397,439 | S | * | 8/1998 | Koros et al. ............... D24/155 |

* cited by examiner

Primary Examiner—David O. Reip
(74) Attorney, Agent, or Firm—Lerner, David, Littenberg, Krumholz & Mentlik, LLP

(57) ABSTRACT

An apparatus for facilitating the fusion of adjacent bone structures includes implant members configured for insertion within a space defined between adjacent bone structures. The device provides a series of resilient supporting arches which serve to act as spacers between two adjacent bone structures. The implant members include a longitudinal portion separated by a plurality of ribs and a lateral chamber used to accommodate various sized spacer rods.

33 Claims, 4 Drawing Sheets

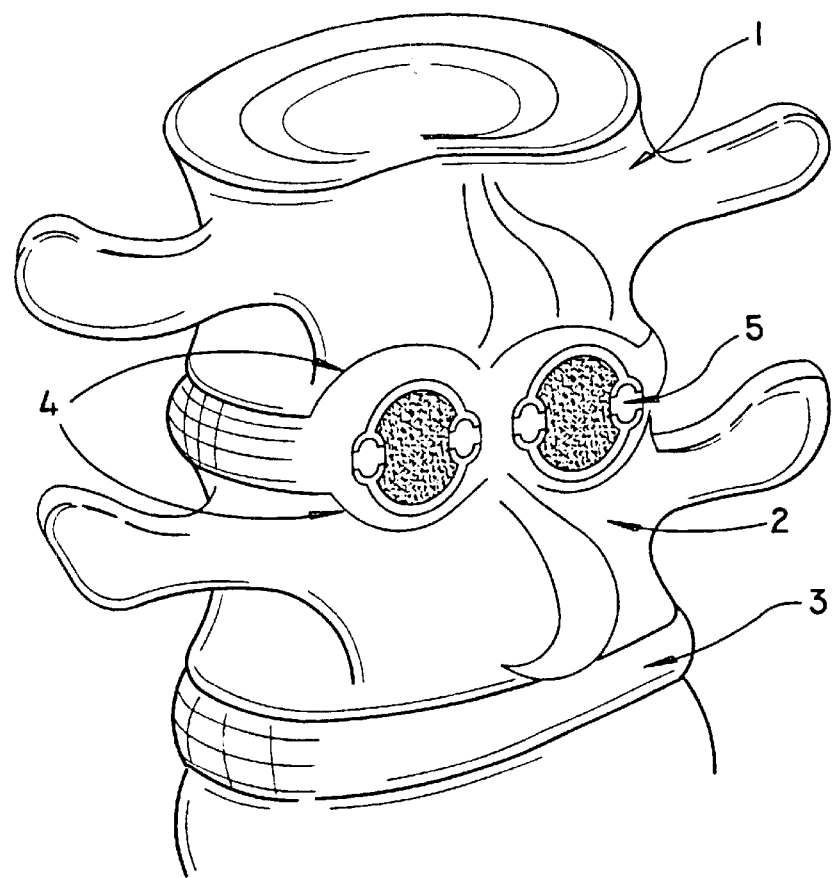
FIG. 1
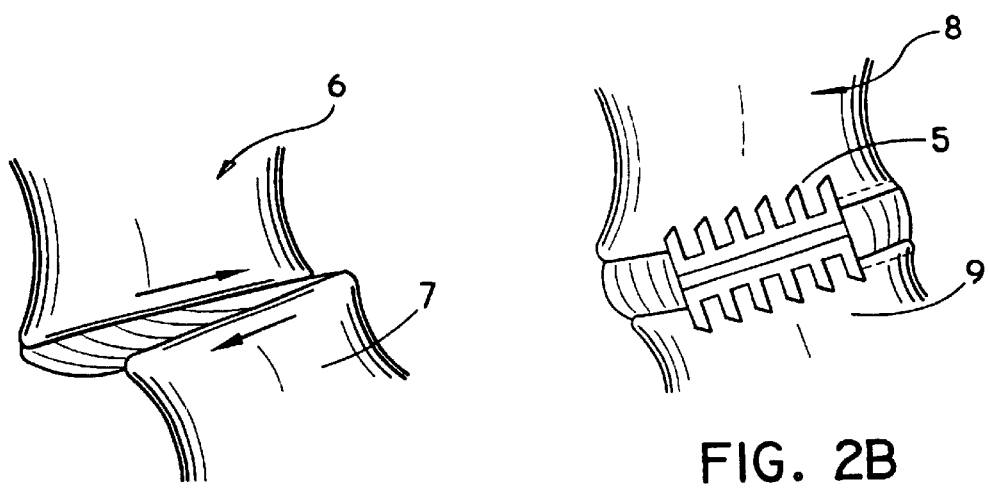
FIG. 2A
FIG. 2B

EXPANDABLE NON-THREADED SPINAL FUSION DEVICE

This application is a continuation of application Ser. No. PCT/US98/02148, filed Feb. 6, 1998, which claims the benefit of provisional application 60/037,458 filed Feb. 6, 1997.

BACKGROUND

1. Technical Field

The present disclosure generally relates to a surgical apparatus and associated methods for fusing two adjacent bone structures such as vertebrae of the spine using an anterior or posterior interbody approach.

2. Background of the Related Art

The deterioration of a body joint such as an intervertebral disc causes the joint space to undergo degenerative changes including narrowing of the joint space and stiffening of the joint. This degeneration of the joint space may lead to mechanical instability of the joint and become severely painful. When no other alternative treatment suffices to stop the disabling pain the joint may have to be fused together.

The fusion process for intervertebral discs typically requires surgically altering the joint surfaces with removal of the articular cartilage and internal tissues attached to the bone. A mechanical device and/or bone material is inserted into the joint to cause the two formerly moving surfaces to fuse or bridge together via the inserted device or bone. Due to various natural effects, bone fusions grow slowly. As such, the bony union may require a period of several weeks or months of bone ingrowth to have sufficient strength to support normal joint loading. The healing period is of course dependent upon such factors as the patient's age, the location of the joint, the forces applied to the joint and the rate by which the bony union progresses in the particular patient. A successful fusion demands that the bone structure of the one bony component of the joint grow together with the bone structure of the second bony component of the joint thereby creating a solid union between these two bony components.

All bones are composed of cortical and cancellous portions, the cortical portion being a thin, hard outer shell and the cancellous portion including an internally soft material. It is known that the most successful fusion promoting substance to be inserted between the two joint components is cancellous or soft bone taken as a graft from a donor site within the patient's body. This soft bone constitutes an autograft and contains growth promoting substances and biochemical materials which accelerate the rate of growth and quality or solidity of the resultant bone fusion. Further, the bone graft material must be supported and stabilized so that it is not subjected to motion or dislocation. During the growth of the bone fusion, a space less than 200 $\mu$M between the bone components and the fusion material will inhibit good bone growth. However, a space of this size or larger permits the ingrowth of fibrous tissue causing the resulting fusion to be poor in strength or to fail to fuse altogether. Along the same lines, motion within the fusing joint or between the bone graft particles will also inhibit bone growth and subsequently inhibit a secure attachment of the bone graft particles to the joint's bony components. In addition, the bone graft material must be brought into contact with a bleeding or vascularized surface of the bone joint to be fused. Since the cancellous inner bone has good intrinsic circulation which is vital to fusion growth, the outer cortical bone must be cut or ground away such that the vascularized cancellous inner bone is exposed and bleeding. It is to this bleeding or vascularized surface that the bone graft is applied.

Proper bone fusion requires that the bone graft material be held firmly in place within the joint space without any excess movement throughout the fusion process. Many methods and devices have been devised to secure the bone graft firmly in place as well as to secure the bony components of the joint in the desired position as the bony fusion slowly develops. Conventional prior art fusion devices are not suitable for the requirements for which the disclosure has been developed. For example, U.S. Pat. No. 4,961,740 to Ray et al. discloses an interbody cage having an internal cavity with an inner surface and an outer surface. A pair of these devices is screwed into parallel round cavities drilled into the adjacent end plates of the vertebral disk bodies. These cavities traverse the end plates of each vertebra penetrating into their cancellous bony vertebral substance. The cavities are then tapped and tight fitting metal cages are screwed into the cavities. The cages hold the bone graft and the vertebral bodies firmly in place. Perforations that face the vertebrae are abundant, up to 70% of the outer surface, but the lateral sides of the cages that face the disc space interposed between the vertebrae are blocked against possible soft tissue ingrowth. Such circular fusion devices must penetrate through the cartilaginous vertebral end plate and into the spongy bone of the vertebral body in order for the bone graft material to grow into the vertebral body and create a solid fusion.

The physical shape, namely the height, of a degenerative vertebral disk is dependent upon its actual state of degeneration. In the less degenerated disc, the diameter of the circular fusion cage must be increased to conform with the disk shape. The maximum diameter of a single cage that can be accepted in a given disc joint is limited by the space between the facet joint or pedicle, laterally, and the posterior disc midline. Thus, there is a limit to which the cage can effectively span the disc in relation to the disk height required and the disk posterior width available. The fusion device of the disclosure allows for an increase in height without a resulting concomitant increase in width.

For successful fusion growth development, the recipient bone surfaces must have the cortical or hard surface portion removed. Beneath this hard surface, the cancellous or soft inner portion of the bone, containing its own circulation will then be exposed to the placement of fusion inducing substances such as cancellous or soft bone from another human (allograft) or from the same patient (autograft). When these fusion inducing substances are first placed within the recipient bone, they have little cohesive strength and therefore are very soft and loosely packed. Therefore, a number of devices and appliances have been developed to hold the bony segments in place under conditions of normal spinal activity and daily stresses. The bone graft material being placed between these segments will slowly reunite the segments. Such devices are not, by themselves, intended to permanently secure immobility of the segments, since bone ingrowth is required to produce the stable fusion.

Dependency on any non-uniting device as the sole stabilizing element may ultimately fail due to the development of mechanical transitions between the bone and the device which will lead to a structural failure of the bone.

Fusion bone material placed between vertebral bodies has been described for some years, but more recently the development of pedicle screw fixation and posterolateral instrumentation has become increasingly popular because of the improvement in percentage fusion rate as compared to the earlier interbody fusion methods. However, the pedicle screw technique has been fraught with a number of problems, particularly related to the patient's safety. Most recently, interbody fusion methods utilizing a bone container, such as a threaded fusion cage, have become increasingly popular because of the improvement in safety and efficacy over other methods and because of lower incidences of complications.

The interbody fusion method is known to be a more efficient technique as compared to methods where bone material is placed around the outside of the vertebral bodies. The interbody fusion is at the center of motion of the spinal segment and requires the least volume of bone to effect a good bone fusion. Further, the fusion enhancing bone material is nearly surrounded by the cortical and/or cancellous bone of the vertebra which provides good nutrition for the fusion growth. For bone material which is laterally placed, nutrition is usually derived from the under surface of the surrounding muscle which is vascularized during the insertion of the fusion device.

The use of cylindrical interbody fusion devices are simpler and safer to implant than are rectangular bone grafts or fusion enhancing devices. To implant a pair of threaded cylindrical fusion devices by a posterior approach, the disc space is entered via two parallel penetrations, one on either side of the central spinous process. Two holes are then drilled or tapped into the interposed disc space and into the adjacent surfaces of the vertebral bones so as to accommodate the two parallel hollow cages. In the case of implanting a pair of threaded cylindrical fusion devices by an anterior approach, two holes are drilled or tapped in close proximity. Screw threads are then cut into the recipient bone bed. The screw threads penetrate into each of the vertebral bodies by a distance of about 3 mm which is sufficient to permit direct contact with vascularized cancellous portion of the vertebrae.

The implantation of a pair of fusion devices is important for stability of the joint space but the method for inserting them must abide by certain anatomical limitations. For example, a singular implant of large diameter of more than 18 to 20 mm cannot be implanted by a posterior approach since the nerves cannot be retracted far enough from either side of the midline to permit such a large device to be safely inserted. The excessive nerve retraction required could readily lead to a nerve stretch injury with damage to nerve function resulting in postoperative severe pain or partial paralysis. Although a range of diameters of the inserts must be available to accommodate disc spaces of different height, fortunately, it has been found that only two different lengths (21 mm and 26 mm) of the implants are needed to accommodate the normal range of vertebral sizes.

The height of the disc space determines the diameter of the insert to be implanted. The distance between the pedicles, from side-to-side across the disc space of the vertebral body ranges from about 30 mm to 45 mm in different sized patients. This distance limits the transverse space available to one or more implants. However, the entire width between the pedicles cannot be used since the vertebrae are oval shaped and the corners of the implants cannot extend outside the vertebral body oval. To do so would otherwise damage or endanger important nerves or major blood vessels that closely approximate the vertebrae. Thus, the combined diameters of a pair of implant devices cannot be wider than about 6 mm less than the overall vertebral body width along the disc level. Therefore, the available practical width usable for a pair of cylindrical implants ranges from about 24 mm to 39 mm. Since each cylindrical implant device must penetrate about 3 mm into each vertebral body so as to contact the cancellous portion of the bone, a disc height equalling or exceeding about 12 mm would require each cylindrical device to be about 18 mm to 20 mm in diameter. However, a pair of such sized devices cannot physically be accepted into a side-to-side arrangement width of the intervertebral disc space. As such, a transversely narrow vertebral segment having a high disc degradation space cannot accommodate two parallel cylindrical implants. Clearly, an improved implant having the ability to increase vertical height without the associated increase in width is needed in the art.

In order for an interbody fusion device to be stable once implanted within the disc space, it is necessary that the device and its implantation technique stretch the anulus fibrosus, the ligamentous band surrounding the outer portion of the disc. The effective elastic recoil effect of this tough ligament plus the patient's body weight and paravertebral muscle tone, collectively, apply considerable force from both vertebral bodies through the implanted fusion implant, thereby stabilizing the device within the intervertebral space. Further, a pair of such cylindrical implants parallelly placed into the disc space provides important segmental stability as the bone fusion grows. This stability must withstand normal lateral flexion-extension and torsional forces applied to the segment. A singular cylindrical implant may provide considerable torsional and flexion-extension stability when implanted parallel to the front-back axis of the disc space, but would not provide adequate stability in lateral side-to-side bending as the segment would hinge over the implant.

The collapse of an implanted cylinder is prevented by two mechanisms, first, the arc of the cage pressing into the vertebral bone includes a distinct compression strength. Secondly, the greater diameter of the implanted cylindrical fusion device is wider than the hole bored into the two vertebrae, that is, the maximum width of the device lies in the disc space inside the vertebral end plates. Therefore, for such a device to further penetrate into either end plate it must stretch the end plate cortical bone. This portion of the cortical bone is the strongest portion of the vertebral body and resists such stretching forces. In actual clinical applications, the implant cages have penetrated into the vertebral bodies by less than 1 mm. The intactness of the cortical edge of the end plate is therefore important to prevention of the collapse of the vertebrae around the implants. A substantial loss in disc space height would be detrimental to the posterior ancillary structures of the spinal segment including the anulus, facet joints and ligaments.

A spherical, expandable spinal implant is disclosed in U.S. Pat. No. 5,059,193 to Kuslich. The Kuslich implant includes deformable ribs which may be expanded outwardly once installed inside the prepared disc space. As a spherical implant, however, it is inherently unstable as was ball bearing type implants disclosed by U. Fernstrom in 1966. The Fernstrom device, intended as an artificial disc, proved to be a non-functional device and most of the several hundred devices implanted had to be later removed.

A spine fusion implant having an oval contour is disclosed in U.S. Pat. Nos. 5,458,638 and 5,489,308 to Kuslich et al. The Kuslich et al. implants include slots along its outer periphery towards the vertebral bodies. The side walls are blocked against invasion of disc material as was described in the literature by Ray. The oval shaped insert requires the drilling of three adjacent holes such that the height is at least twice the width. This concept addressed the same limitations in disc width space versus disc height space as discussed above. The Kuslich et al. implants are not expandable and any potential combination of increased height plus expandability are not disclosed by the Kuslich et al. references.

Furthermore, the Kuslich et al. patents dislose that the semi-cylindrical arcuate ribs are not tapered for the purpose of prevention of expulsion or pullout after insertion into the prepared disc space, but rather to promote ease of insertion without concern for expulsion except as may be provided by the settling of vertebral spongy bone into the slots between the ribs.

The expandable non-threaded spinal fusion device of the disclosure overcomes the difficulties described above and affords other features and advantages heretofore not available.

SUMMARY

The device disclosed herein provides a series of resilient supporting arches which act as spacers between the two vertebral bodies, but also permit a simple partial collapse of about 1 mm of soft bone into the spaces between the arches. These arches preferably have parallel slots machined perpendicular to the long access of the implanted device. After insertion of the device, a combination of body weight and muscular contractions applied across the vertebrae and device serve to allow the vertebral bone to descend or sink into the parallel slots of the device. The vertebral bone will descend or sink across the device to a point that will allow fusion promoting substance, i.e. bone material or any of the well known substitutes such as bone morphologic protein, hydroxyapatite or bone growth factor, placed within the slotted arches to be brought into contact with the bone of the vertebral body. Furthermore, the device can be made in a narrow range of sizes since the two halves of the device are placed into a hole bored between the vertebral bodies and then the halves of the device are forced apart to penetrate into the softer bone of the vertebral spongiosa or cancellous bone. Thus, both the width and height of the devices are separately controlled.

The cortical portion of the juxtaposed end plate of the vertebra is cut away by a drilling process thereby forming the hole which will accommodate the two halves of the slotted cage. An insertion tool or spreading device delivers the two halves of the cage inside the hole and then spreads the two halves apart to force the parallel ribs of the cage into the recipient soft bone.

The spreading device elevates and/or separates the two halves of the cage until the outer anulus of the cage becomes abutted tightly against the receiving bone and capable of exerting sufficient counter force to stabilize each of the slotted cages. While being spread apart by the spreading device, notched rod-like spacers of various heights may then be inserted into the lateral stabilizing structures or channels of each cage. Once the notched spacers are inserted, the spreading device is released and removed from within the two halves of the cage. At this time, the recoil force of the outer anulus of the cage will force the lateral portions of each cage against the spacers further stabilizing them.

In addition, the insertion tool is capable of moving either one of the cage halves further out of or further into the drilled holes of the vertebral body in order to compensate for any slippage between the two vertebral bodies which may have occurred as a result of injury or degeneration. Once the two halves of the cage are situated in the drilled holes of the vertebral body, the insertion tool can then be used to correct the slippage and alignment before the notched spacers are placed. After properly aligning the vertebral bodies, the notched spacers are inserted and positioned along the lateral stabilizer channels of the cage. The insertion or spreading tool is then removed allowing the recoil of the outer anulus of the cage to force the ribs of the slotted arches into the bone, thereby stabilizing the now corrected displacement of the vertebral bodies.

This unique system, therefore, allows for an assortment of diameters of the cages to satisfy a wide variety of heights of the disc spaces. Other objects and advantages of this structure will become apparent from the following detailed description and from the appended drawings in which like numbers have been used to describe like parts throughout the several views.

BRIEF DESCRIPTION OF THE DRAWINGS

Preferred embodiments of the present disclosure are described herein with reference to the drawings wherein:

FIG. 1 is a view from the posterior aspect of two adjacent vertebral bodies and the fusion implant device of the disclosure;

FIG. 2A is a view from a lateral aspect illustrating two adjacent misaligned vertebrae;

FIG. 2B is a view from a lateral aspect illustrating two correctly aligned vertebrae using the fusion implant device of the disclosure;

DETAILED DESCRIPTION OF PREFERRED EMBODIMENTS

Figure 3A:
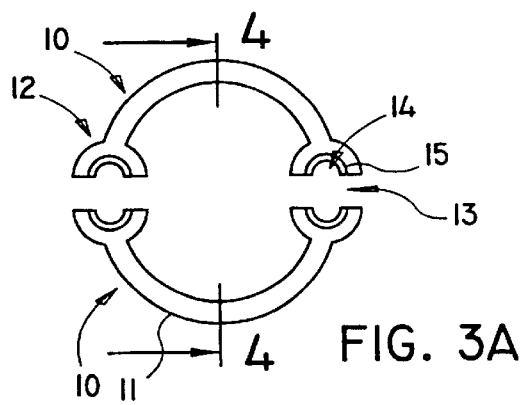
FIG. 3A is a cross-sectional view of the slotted two fusion implant halves and lateral stabilizers.

The preferred embodiments of the apparatus and methods disclosed herein are discussed in terms of orthopedic spinal fusion procedures and instrumentation. It is envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion includes a description of the spinal fusion implant utilized in performing a spinal fusion followed by a description of the preferred method for spinal fusion in accordance with the present disclosure.

In the discussion which follows, the term "proximal", as is traditional, will refer to the portion of the structure which is closer to the operator, while the term "distal" will refer to the portion which is further from the operator.

Referring now to the drawings in which like reference numerals identify similar or identical elements throughout the several views, FIGS. 3–5 and 9 illustrate, in perspective, the fusion implant device of the disclosure. Fusion implant device 5 is contemplated to be a self-tapping implant, i.e., the implant is intended to be inserted within a preformed bore in adjacent bone structure, e.g., adjacent vertebrae, without necessitating tapping of an internal thread within the bone structures prior to insertion. Fusion implant device 5 is preferably fabricated from a suitable bio-compatible rigid material such as titanium and/or alloys of titanium, stainless steel, ceramic materials or rigid polymeric materials. It is also contemplated that fusion implant device 5, at least partially, be fabricated of bioabsorbable materials.

With reference to FIG. 1, disk vertebrae 1, 2 and an implanted fusion implant device 5 according to the disclosure is shown. A posterior aspect of the two adjacent vertebral disks 1, 2 include a pair of fusion implants 5 containing inserted rod-like spacer inserts 16, 17, 18 and bone fusing material 27 contained therein. The fibers of the ligamentous anulus 3 and the bilateral laminectomies are preformed through the posterior bony structure 4 which surround the fusion implants 5.

As is best depicted in FIGS. 2A and 2B, vertebrae disc 6 is misaligned with respect to vertebrae disc 7 in that disc 6 has slipped forward relative to disc 7. The direction of force necessary to correct the slippage is shown by the opposing arrows near the ligamentous anulus space between the vertebral discs. With the use of the fusion implant device 5 and methods disclosed in the disclosure, it is possible to correct such misaligned discs as is shown in FIG. 2B. Vertebrae discs 8 and 9 are corrected relative to each other with the use of the fusion implant device 5 and are now in proper anatomical alignment.

Figure 3B:
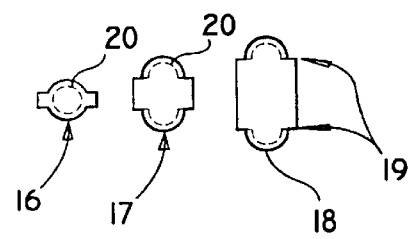
FIG. 3B is a cross-sectional view of various sized notched spacer rods.
Figure 9:
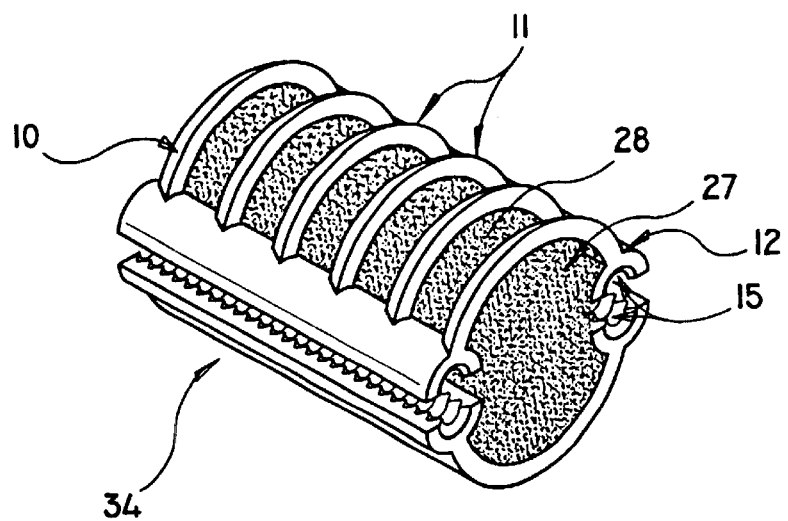
FIG. 9 is a view illustrating the slotted fusion implant halves encasing a core of the bone fusion inducing substance.

With reference to FIGS. 3A and 3B, the fusion implant device 5 includes slotted fusion implant halves 10 and their respective lateral stabilizers 12 to which the arches of the fusion implant device 5 are provided in the form of spaced apart slotted ribs 11. The union of the slotted fusion implant halves 10 form a fusion cage 34, as is shown in FIG. 9. As shown in FIG. 3A, the lateral stabilizers 12 include a semi-circular outer periphery, however, the lateral stabilizers 12 could also include a less arcuate or horizontal outer periphery thereby allowing the cortical plates to rest upon the lateral stabilizers and further prevent the lateral collapse of the vertebral bodies. Notches 15 line the interior portion of the lateral stabilizer portions 12 along the lateral stabilizer channels 14. The notches 15 of the lateral stabilizers 12 correspondingly engage with notches 20 of the various sized rod spacers 16, 17, 18 when inserted into the lateral stabilizer channels 14. It is to be contemplated that the notches 15 of the lateral stabilizer portions 12 and the notches 20 of the spacers 16, 17, 18 can include like engagement apparatuses such as threads, ribs, teeth or facets. The space 13 between the lateral stabilizer portions 12 is spread apart to accommodate the various heights of spacers 16, 17, 18. In operation, the notches 15 of the lateral stabilizers 12 engage the notches 20 of the spacers 16, 17, 18 and form a single unitary cage 34. The spacers 18 include lateral shoulders 19 which are designed to resist collapse of the fusion implant cage 34 when under a crushing force. After the two implant halves 10 of the fusion implant device 5 have been used to correct the slippage between two vertebrae, the crushing force applied between the notches 15 of the stabilizers 12 and the notches 20 of the spacers 16, 17, 18 will not allow the two vertebra from slipping back into the original misaligned or abnormal position. The spacer inserts 16, 17, 18, as well as the fusion implant halves 10 may also be made of a bioabsorbable material so that they will slowly dissolve as the bone fusion between the two vertebral bodies continues to grow. In doing so, the spacer inserts 16, 17, 18 will slowly transfer the forces resisting collapse back to the resulting bone graft or fusion. Thus, as the bone graft or fusion continues to grow, it will gradually take over the load forces and thereby enhance the growth and overall strength of the resulting graft or fusion.

Figure 4:
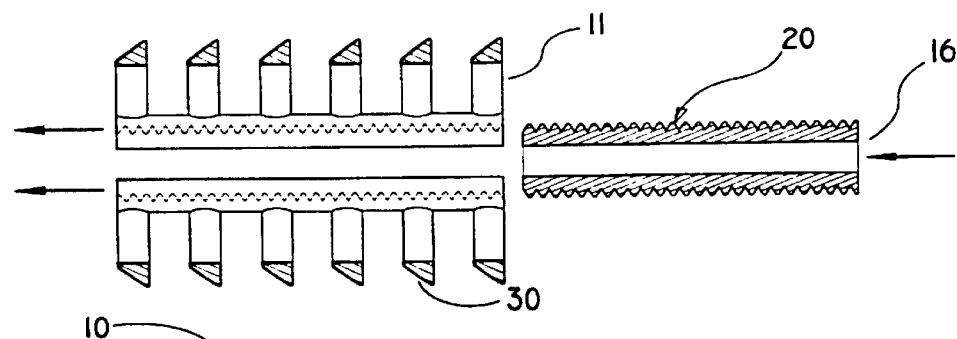
FIG. 4 is a longitudinal cross-section of the two slotted fusion implant halves and a corresponding spacer rod.

As is best depicted in FIG. 4, the mating relationship between the spacer 16 and the two fusion implant halves 10 is shown. The two fusion implant halves 10 include ribs 11 having sloped surfaces 30 designed to prevent expulsion or pullout of the fusion implant halves 10 under force. The sloped surfaces 30 of the ribs 11 may vary in degree to a slope which is dependent upon the amount of force expected to act upon the inserted fusion device 5. Once chosen for appropriate height, spacer 16 showing notches 20 is inserted into the space 13 between the lateral stabilizer portions 12. Spacer 16 including notches 20 will then be matingly fitted with the notches 15 of the lateral stabilizer portions 12.

Figure 5:
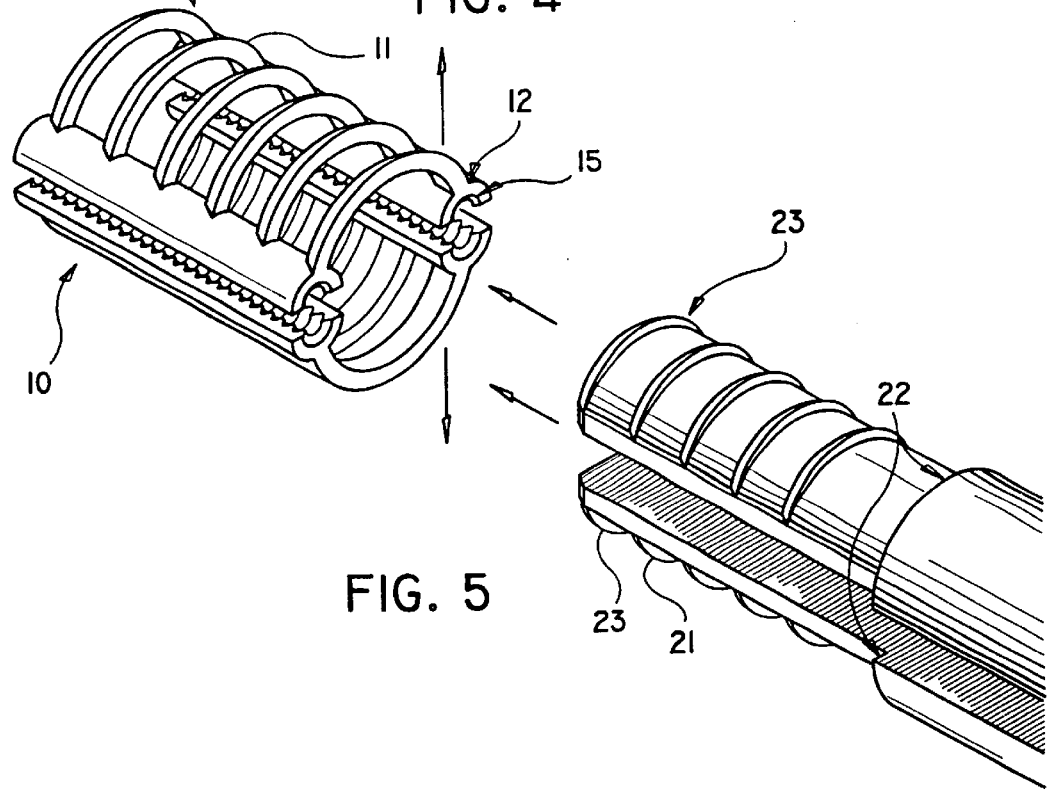
FIG. 5 is an exploded isometric view of the slotted fusion implant halves and the insertion-distraction tool.
Figure 6:
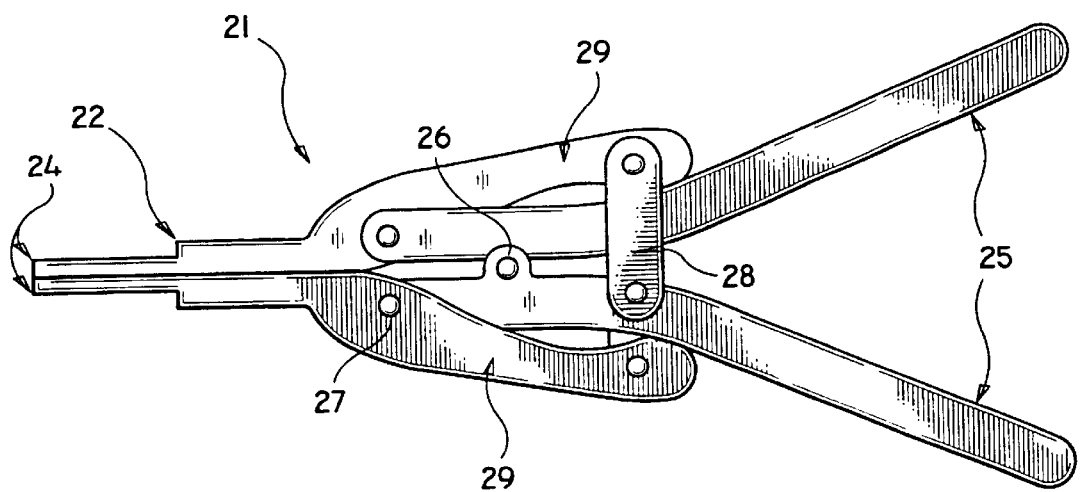
FIG. 6 is a side planar view of the insertion-distraction tool in the closed position.
Figure 7:
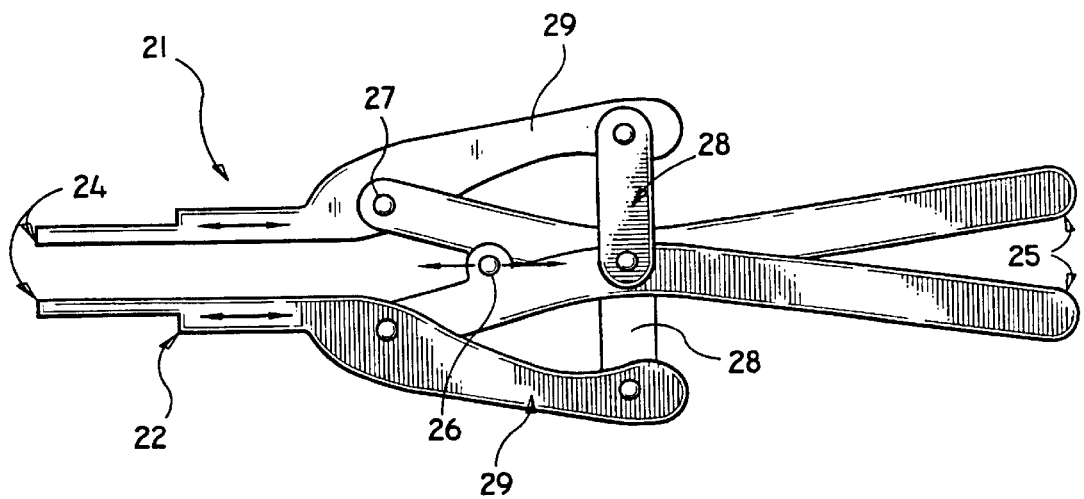
FIG. 7 is a side planar view of the insertion-distraction tool in the open position.

With reference to FIGS. 5–7, insertion-distraction tool 21 is designed to accommodate the various potential lengths of fusion implant halves 10. Insertion-distraction tool 21 includes limit stops 22 which prevents tool 21 from being over inserted into the fusion implant halves 10. The tool 21 includes lateral retaining ribs 23 which are designed to grab the internal portion of slotted ribs 11 of fusion implant halves 10. The lateral retaining ribs 23 allow for the insertion-distraction tool 21 to be displaced relative to each other in order to permit realignment of slippage of one vertebra disc relative to another vertebrae disc.

The insertion-distraction tool 21, as shown in FIG. 6, includes handles 25 which are normally displaced apart from one another when the insertion-distraction tool 21 is in a resting or spread apart position. In this resting position, the tool tips 24 are positioned closed so that the tool 21 may be inserted within the fusion device halves 10. In operation, tool tips 24 are inserted within the fusion device halves 10 until limit stops 22 abut against a proximal slotted rib 11. The central hinge point 26 of tool 21 defines the motion of the handles 25 moving extension mass 29 of the tips 24 around hinge points 27 which causes spreading apart or closing of the tips 24. Two cross members 28 articulate with extension masses 20 to maintain tips 24 parallel with respect to one another when being spread apart by the actuation of handles 25.

The insertion-distraction tool 21, as shown in FIG. 7, includes handles 25 which are in a closed position, which are spread apart in a parallel relationship. In this position the tips 24 are used to spread the fusion implant halves 10 in a manner parallel to the cortical end plates of the vertebral bodies. A means to shift the location (not shown) of the hinge point 26 would allow the tips 24 to open in a slightly non-parallel fashion as may be needed for the final positioning of the fusion implant halves 10. A ratchet locking means (not shown) to hold the handles 25 in the desired position can be provided to maintain the spreading of the vertebral disc space as the fusion implant halves 10 are positioned.

Figure 8A:
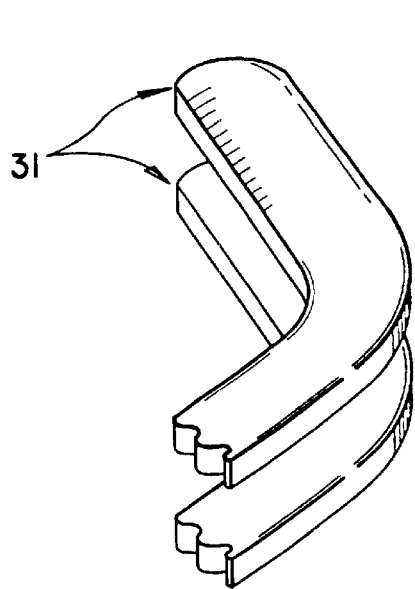
FIG. 8A is a view illustrating an alternative embodiment of the insertion-distraction tool tip.
Figure 8B:
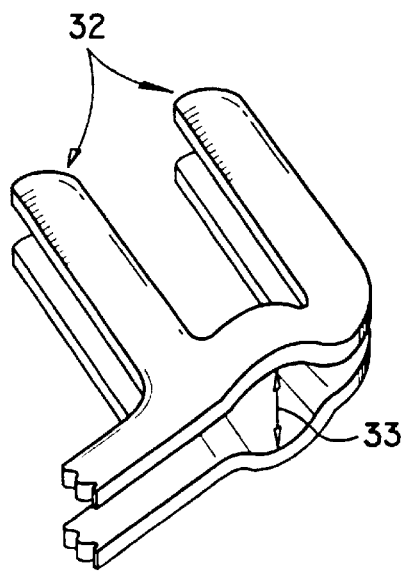
FIG. 8B is a view illustrating an alternative embodiment of the insertion-distraction tool tip.

With reference to FIGS. 8A and 8B, alternate embodiments of the insertion-distraction tool 21 are shown. A single pair of broad tips 31 can be used to spread the central core of the fusion implant halves 10 into the vertebral bone. In an alternative embodiment, a dual pair of narrower tips or blades 32 can be used within the lateral stabilizer channels 14 to spread the fusion implant halves 10. The blades 32 include a central bow 33 which are designed to permit the passage of a central core preform of fusion inducing substance 27.

A pair of slotted fusion implant halves 10 including supporting ribs 11 and lateral stabilizer shoulders 12 are shown in FIG. 9. The insertion-distraction tool 21 with paired tips 24 or 31 or 32, as discussed above, engages the notches 15 of the lateral stabilizers 12 on both sides of the fusion implant halves 10 spreading them apart to permit the insertion of a preformed porous solid core of fusion inducing substance 27. The porous core 27 may be preformed so that semicircular ridges on the external periphery of the porous core 27 project into and out of corresponding slots 28 between the ribs 11 of the fusion implant halves 10. The porous core 27 is of sufficient strength to withstand the compressive forces between the vertebral bodies as the fusion of the bones develops. Porous cores 27 of various sizes are used to accommodate various disc heights. A temporary spacer porous core (acting simply as a spacer) may be initially placed on one side of the vertebral bodies for partial spreading of the disc space. The second vertebral side will then receive a full height porous core 27. Finally, returning to the first side of the vertebral bodies, the temporary spacer porous core is removed and a permanent porous core 27 is placed within the disc space between the fusion implant halves 10. For further stabilization, if needed, appropriately shaped rods, screws or other similar spacing-type apparatuses may be driven into the lateral stabilizer channels 14 and driven along the length of the stabilizers 12 to add the needed stabilization throughout the implant procedure.

A preferred embodiment of the present fusion implant system includes a slotted fusion implant device 5 to be implanted in and promote fusion with respect to one or more bone structures wherein the fusion implant system contains a bone fusion inducing substance 27, such as bone material, bone morphologic protein, hydroxyapatite or bone growth factor, packed therein. Preferably, the fusion implant system includes a fusion implant having two halves 10 consisting of slotted arches or ribs 11 having an outside radius and an inside radius with deep complete perforations between the arches 11 where the outer portion and inner portion of the arches 11 become confluent. The fusion implant system also includes lateral notched spacer rods 16, 17, 18 having a semi-circular outer periphery that attach along the longitudinal axis of the lateral stabilizers 12 providing a base for them. Also, dependent on the shape of the corresponding lateral stabilizers 12, the spacer rods 16, 17, 18 could include a less arcuate or horizontal outer periphery. The lateral stabilizers 12 have threads or notches 15 along their internal diameters extending along the length of the fusion implant 5. As shown in FIG. 4, the circular ribs 11 have slopes of 30 degrees to 45 degrees relative to the longitudinal axis of the fusion implant 5 providing additional resistance to axial displacement or expulsion of the fusion implant halves 10.

Upon placement of both fusion implant halves 10 opposite to each other within a bore drilled between two vertebral bodies, the fusion implant halves 10 may be forced apart so that the circular ribs 11 are forced into the softer cancellous bone of the vertebral bodies, thus stabilizing the fusion implant halves 10 within each opposing vertebral body. Lateral stabilizers 12 containing threads or notches 15 are used to accommodate notched rod spacers 16, 17, 18 of various heights that are placed after the fusion implant halves 10 are forced apart in order to maintain the new distracted height of the vertebral bodies after the fusion implant halves 10 have been implanted.

The internal cavity of the two fusion implant halves 10 will accommodate a fusion growth inducing substance 27 either as a preformed core or as separate morsels and protect that substance from extrusion or collapse by the semi-circular ribs 11 of the fusion implant halves 10. Once the fusion implant halves 10 have been fully distracted and the semi-circular ribs 11 have penetrated into the vertebral bodies, notched spacer rods 16, 17, 18 are placed laterally along the lateral stabilizers 12 wherein the notches 20 of spacers 16, 17, 18 engage the notches 15 of the lateral stabilizers 12, thus holding the fusion implant halves 10 firmly apart and preventing axial displacement of the two halves 10 relative to each other's position.

The fusion implant system is installed with an insertion-distraction tool 21 capable of separating the two fusion implant halves 10 to the appropriate distraction which allow for the placement of spacers 16, 17, 18 before removal of the tool. The tool 21 preferably has two halves, as shown in FIG. 5, with each half having notches or prominences 23 around their diameter that engage the internal rib structure 11 of the fusion implant halves 10 to prevent their displacement relative to the tool 21. The two halves of the insertion-distraction tool 21 may be axially displaced relative to each other in order to move the position of the fusion implant halves 10 and thereby the now attached vertebral bodies for the purpose of realignment of a displacement of the two vertebral bodies relative to each other. The tool 21 includes jack-like scissor linkage, as described earlier, to keep the jaw-like tool halves and tips 24 generally parallel.

The fusion implant system of the present disclosure, therefore, has the novel ability to adapt to varying vertebral bodies as to the softness of their bone, width of the disc space and then to allow sufficient corrective force to permit realignment of the pathologically displaced vertebra.

In operation, the novel fusion implant system can be implanted by the following method using a standard surgical approach as though a laminectomy or discectomy is to be performed on either side of the vertebral body. Prior to the act of drilling bore holes in the vertebral bodies, the nerve structures are displaced first to one side and then to the other side in order to avoid contact with the intervertebral drill. Two bore holes are drilled to the appropriate depth, extending at least 75% of the total intradiscal front to back diameter. The bore holes should penetrate through the end places bilaterally and be between 1 to 3 mm in depth into the cancellous portion of the vertebral bodies. The bore holes would normally be between 10–14 mm in diameter. The two arched halves 10 of the fusion implant device 5 are then mounted on the insertion-distraction tool 21 and inserted into one of the drilled holes. One drill hole is fitted with the fusion implant device 5 and then the other drill hole is similarly fitted. The insertion-distraction tool 21 seats the fusion implant device 5 deeply within the hole to a point where the tool 21 abuts against the posterior margin of the hole, as determined by the limit stops 22 which are machined on the tool 21. Distraction of the tool 21 then forces the sloped surfaces or sharpened edges 30 of the ribs 11 of the implant halves 10 deeply into the cancellous bone. Further, the distraction tool 21 spreads the space until the anulus of the fusion implant device 5 is quite firmly seated and within normal intervertebral distance. Appropriate elongated spacers 16, 17, 18 are then inserted into the space 13 between the lateral stabilizers 12 engaging small notches 15 within the lateral channels 14 to prevent slippage of one fusion implant half 10 relative to the other along the common axis of penetration. The height of the spacers 16, 17, 18 is chosen to provide sufficient firmness to the anulus where a counter force will then hold the fusion implant halves 10 and its lateral spacers 16, 17, 18 in firm axial alignment relative to each other. The tool 21 is then released and removed allowing the full outer anulus force to be exerted against the fusion implant halves 10 and the spacers 16, 17, 18. The cage 34 is then packed with an appropriate amount of bone fusion inducing substance 27 such as an autograft or allograft. A ceramic insert may be fitted for the cage 34 or small portion of hydroxylapatite may be packed inside the cage 34. This packing of the fusion inducing material 27 further provides strength so as to resist the potential collapse of the cage 34 or the over penetration of the slotted ribs 11 into the recipient bone bed.

An additional method for the surgical procedure would best be used on patient's having a degenerative or traumatic slippage of one vertebra upon the other. In this case, the procedure would be different, in that, after the elevation or spreading of the implant halves 10, one portion of the insertion tool 21 would then slide inward or rearward relative to the other implant half 10 and insertion tool 21 so that the bone into which the implant half 10 has been inserted may be realigned relative to each other along their anterior-posterior axes. Once repositioned, the system should be sufficiently stable to resist re-slippage or misalignment after the tool 21 has been removed. This procedure may require that one implant half 10 be inserted deeper relative to the other before the realignment process begins. After spreading the space and forcing the implant halves 10 into the recipient bone beds the halves 10 and the attached vertebral bodies would be appropriately repositioned. This corrected position would be secured by effectively locking the notched portions 15 of the lateral stabilizers 12 into the notched portion 20 of spacer rods 16, 17, 18. The notches 20 the spacer rods 16, 17, 18 would be forced tightly into the corresponding notches 15 of the lateral stabilizers 12 by the forces of the anulus recoil and body weight of the patient. These forces would prevent the now corrected vertebral alignment from any further slippage.

A further method uses a spreader means to elevate the two sides of a semicircular fusion insert half 10 by its transverse slots 28 such that a suitable fusion core insert 27 may be installed inside the central core of the fusion implant cage 34. This method provides that the lateral slots 28 be elevated while a central core insert 27 of correct height is placed within the fusion implant halves 10. This core insert 27 should be made of a porous bone growth inducing substance to create a fusion between the core substance and the vertebral body bone beds which are apparent across the slots 28. This method may use a preformed core 27 of sufficient strength to support the vertebral load during fusion development. This current method is in contrast with the previously discussed method which requires the packing of morsels of fusion inducing substance 27 after the fusion implant device 5 is placed within the vertebral bodies. Lateral transverse notched spacer rods 16, 17, 18 may additionally be placed if further stability is needed. The preformed insert 27 may have mating grooves to fit within the slots 28 of the fusion implant 5 to partially fill the slots 28 and provide additional anterior-posterior resistance to slippage (spondylolisthesis). When a preformed core 27 is used having semicircular elevations to match the fusion insert slots 28; the implant halves 10 may be independently repositioned using the appropriate insertion-distraction tool 21 to correct any slippage. The mated elevations and grooves of the preformed core 27 then serve as a means to prevent a return to the slipped or misaligned position.

In operation, the alternative embodiments and methods of the fusion implant system can be implanted by the following method using a standard surgical approach as though a laminectomy or discectomy is to be performed on either side of the vertebral body. Prior to the act of drilling bore holes into the vertebral bodies, the nerve structures are displaced first to one side and then to the other side in order to avoid contact with the intervertebral drill. Two bore holes are drilled to the appropriate depth, extending at least 75% of the total intradiscal front to back diameter. The bore holes should penetrate through the end plates bilaterally and be between 1 to 3 mm in depth into the cancellous portion of the vertebral bodies. The bore holes would normally be between 10–14 mm in diameter. The lateral slots 28 of the two arched halves 10 of the fusion implant device 5 are then mounted on the insertion-distraction tool 21 and inserted into one of the drilled holes. One drill hole is fitted with the fusion implant device 5 and then the other drill hole is similarly fitted. The insertion-distraction tool 21 seats the fusion implant device 5 deeply within the hole to a point where the tool 21 abuts against the posterior margin of the hole, as determined by the limit stops 22 which are machined on the tool 21. Distraction of the tool 21 then forces the sloped surfaces or sharpened edges 30 of the ribs 11 of the implant halves 10 deeply into the cancellous bone. Further, the distraction tool 21 spreads the space until the anulus of the fusion implant device 5 is quite firmly seated and within normal intervertebral distance. A preformed core 27 of appropriate size is then inserted into the central cavity of the fusion implant device 5. This core exerts force against the ribs 11 of the slotted fusion insert halves 10 which in turn force the ribs 11 into the vertebral bone bed. The correct height of the core provides sufficient firmness to the anulus where a counter force will then hold the fusion implant halves 10 in firm axial alignment relative to each other. The tool 21 is then released and removed allowing the full outer anulus force to be exerted against the fusion implant halves 10 and the preformed core 27.

When the relationship between the two adjacent vertebral bodies is considerably altered, any of the procedures above may be performed incrementally. That is, part of the needed correction or realignment may be performed temporarily on one side with the placement of an intermediate sized spreading or correcting insert. That first side with its intermediate correction is then temporarily abandoned while a fully correcting insert is permanently placed on the second side. Then, returning again to the first side, the temporary partial correcting insert is removed and replaced with a permanent insert equal to the one on the second side, thereby fully correcting or realigning the two vertebrae. Effectively, this method permits a more gradual change in the misalignment which at times may be necessary as the collagen fibers of the ligamentous anulus of the disc sometimes stretch slowly and an initial attempt at full correction on only the first side may cause tearing of these fibers or fracture of the vertebral bone.

It will be understood that various modifications may be made to the embodiments disclosed herein. For example, the fusion implant device may incorporate more than two fusion implant sections within a single bore or the external ribs may include a pointed edge with a slope greater than 45 degrees. Therefore, the above description should not be construed as limiting, but merely as exemplifications of preferred embodiments. Those skilled in the art will envision other modifications within the scope and spirit of the claims appended hereto.

What is claimed is:

1. A fusion implant system for promoting fusion of adjacent bone structures wherein the fusion implant system contains a bone fusion inducing substance packed therein, the fusion implant system comprising:
    a fusion implant having at least two separable sections, each section including arches and at least two lateral stabilizers having a longitudinal axis transverse to the arches.

2. The fusion implant system according to claim 1, wherein the lateral stabilizers include channels along the longitudinal axis and the arches include slots.

3. The fusion implant system according to claim 2, further including at least one spacer to be matingly received within the channels of each lateral stabilizer.

4. The fusion implant system according to claim 3, wherein the at least one spacer includes a set of various sized spacers for varying a distance between the at least two sections.

5. The fusion system according to 3, wherein the at least one spacer further includes engagement apparatus along its transverse outer periphery.

6. The fusion implant system according to claim 5, wherein the channels further include engagement apparatus along their transverse inner periphery.

7. The fusion implant system according to claim 6, wherein the engagement apparatus of both the channels and the spacers engage each other when the fusion implant system is implemented.

8. The fusion implant system according to claim 1, wherein the system is made at least partially from a bioabsorbable material.

9. The fusion implant system according to claim 1, wherein the fusion implant is adapted to be placed within a bore drilled between the two adjacent bone structures and wherein the fusion implant is adapted to be pressed against surrounding walls of the bore so that the arches are pressed into the surrounding walls of the bore.

10. The fusion implant system according to claim 9, wherein the at least one spacer is interposed within the channels of the lateral stabilizers, wherein the spacers are chosen to correspond to a particular height between the fusion implant pressed against the walls of the bore.

11. A method for fusion of adjacent vertebrae having a disk space therebetween, the method comprising the steps of:
    accessing the disk space and forming a bore therein;
    implanting a fusion implant device within the bore, the fusion implant device including at least two sections, each section including arches and at least two lateral stabilizers having a longitudinal axis transverse to the arches, each lateral stabilizer having a channel along the longitudinal axis;
    positioning the at least two sections of the fusion implant within the bore so that the arches penetrate the bone material of the adjacent vertebrae and defining a core area therebetween; and
    inserting a spacer along the channel of each lateral stabilizer.

12. The method according to claim 11 wherein the step of positioning includes:
    inserting an insertion tool within the bore, the insertion tool including a handle and a tip structure, the tip structure being received within the bore; and
    expanding the tip structure within the bore against the at least two sections of the fusion implant thereby forcing the arches into adjacent bone material.

13. The method according to 11, further comprising the step of packing the core area with fusion promoting material.

14. The method according to 11, wherein the channels of the lateral stabilizers and the spacers include mating apparatus to thereby enhance engagement of the lateral stabilizers and the spacers during the inserting step.

15. The method according to 11, wherein the spacer further includes a set of various sized spacers for varying a distance between the at least two sections.

16. A nonthreaded fusion implant system to be implanted in and promote fusion within one or more bone structures, wherein the fusion implant system contains a bone fusion inducing substance packed therein, the fusion implant system comprising:
    a fusion implant comprising two halves, each half including arches having an outside portion and an inside portion, wherein the outside portion and the inside portion meet at a confluent edge;
    lateral stabilizers positioned along a longitudinal axis of each fusion implant half, the lateral stabilizers having notches or threads along an internal periphery along the longitudinal axis;
    slotted spacers positioned along the longitudinal axis of the lateral stabilizers; and wherein the confluent edges of the arches include a slope between 30 and 45 degrees relative to the longitudinal axis of the fusion implant halves.

17. The nonthreaded fusion implant system according to claim 16, wherein the halves of the fusion implant are positioned within a bore within the bone structures and wherein the halves are forced apart so that the arches are pressed into soft surrounding bone of the bone structures.

18. The nonthreaded fusion implant system according to claim 17, further comprising notches or threads along a portion of the outer periphery of the slotted spacers, and wherein the slotted spacers are positioned within the lateral stabilizers to maintain a desired distracted and axial position between the fusion implant halves.

19. The nonthreaded fusion implant system according to claim 18, further comprising a protective cavity formed between the fusion implant halves once in the distracted and axial positions, wherein the bone fusion growth inducing substance is placed within the protective cavity.

20. The nonthreaded fusion implant system according to claim 18, further comprising an insertion tool having a tip section which is capable of the forcing apart of the fusion implant halves so that slotted spacers may be positioned within the lateral stabilizers.

21. The nonthreaded fusion implant system according to claim 20, wherein the tip of the insertion tool further includes notches to engage the fusion implant halves between the arches to thereby prevent the fusion implant halves from being displaced with respect to the insertion tool during the positioning of the fusion implant halves within the bore.

22. The nonthreaded fusion implant system according to claim 20, wherein the tip section of the insertion tool further includes dual tips separated along a longitudinal axis of the insertion tool, wherein each tip can be axially displaced relative to each other along the longitudinal axis of the insertion tool.

23. The nonthreaded fusion implant system according to claim 20, wherein the tip section of the insertion tool further includes separate blade sections to be inserted along the longitudinal axis of each lateral stabilizer, the separate blade sections forming a bow section therebetween capable of allowing the bone fusion growth inducing substance to be inserted through the bow section.

24. The nonthreaded fusion implant system according to claim 16, wherein the bone fusion growth inducing substance is a force bearing porous preformed core insert.

25. A fusion implant system for promoting fusion of adjacent bone structures wherein the fusion implant system contains a bone fusion inducing substance packed therein, the fusion implant system comprising:

a fusion implant having at least two sections, each section including arches, and at least two lateral stabilizers having a longitudinal axis transverse to the arches, wherein the lateral stabilizers include channels along the longitudinal axis and the arches include slots.

26. The fusion implant system according to claim 25, further including at least one spacer to be matingly received within the channels of each lateral stabilizer.

27. The fusion implant system according to claim 26, wherein the at least one spacer includes a set of various sized spacers for varying a distance between the at least two sections.

28. The fusion implant system according to claim 26, wherein the at least one spacer further includes engagement apparatus along its transverse outer periphery.

29. The fusion implant system according to claim 28, wherein the channels further include engagement apparatus along their transverse inner periphery.

30. The fusion implant system according to claim 29, wherein the engagement apparatus of both the channels and the spacers engage each other when the fusion implant system is implemented.

31. The fusion implant system according to claim 25, wherein the system is made at least partially from a bioabsorbable material.

32. The fusion implant system according to claim 25, wherein the fusion implant is adapted to be placed within a bore drilled between the two adjacent bone structures and wherein the fusion implant is adapted to be pressed against surrounding walls of the bore so that the arches are pressed into the surrounding walls of the bore.

33. The fusion implant according to claim 32, wherein the at least one spacer is interposed within the channels of the lateral stabilizers, wherein the spacers are chosen to correspond to a particular height between the fusion implant pressed against the walls of the bore.

* * * * *

UNITED STATES PATENT AND TRADEMARK OFFICE
CERTIFICATE OF CORRECTION

PATENT NO. : 6,582,431 B1
DATED : June 24, 2003
INVENTOR(S) : Charles Ray Dean

It is certified that error appears in the above-identified patent and that said Letters Patent is hereby corrected as shown below:

Title page,
Item [63], "PCT/US99/02148" should read -- PCT/US98/02148. --

Column 3,
Line 17, "vertebra" should read -- vertebrae --.

Column 13,
Line 20, before "3" insert -- claim --.

Column 14,
Lines 1, 3 and 7, before "11" insert -- claim --.

Signed and Sealed this

Seventh Day of October, 2003

JAMES E. ROGAN
*Director of the United States Patent and Trademark Office*